United States Patent

Mertins

[11] Patent Number: 6,046,460
[45] Date of Patent: Apr. 4, 2000

[54] LIGHT CURING DEVICE

[75] Inventor: Jurgen Mertins, Numfeld, Switzerland

[73] Assignee: Ivoclar AG, Schaan, Liechtenstein

[21] Appl. No.: 09/098,553

[22] Filed: Jun. 17, 1998

Related U.S. Application Data

[63] Continuation-in-part of application No. 08/749,602, Nov. 18, 1996, abandoned.

[30]  Foreign Application Priority Data

Nov. 17, 1995 [DE] Germany ............... 195 42 985

[51] Int. Cl.[7] ....................................................... G01J 1/00
[52] U.S. Cl. ................... 250/504 H; 250/504 R
[58] Field of Search ...................... 250/504 H, 504 R

[56] References Cited

U.S. PATENT DOCUMENTS

| 4,112,335 | 9/1978 | Gonser | 315/241 R |
|---|---|---|---|
| 4,229,658 | 10/1980 | Gonser | 250/504 H |
| 4,292,664 | 9/1981 | Mack | 362/120 |
| 4,298,806 | 11/1981 | Herold | 250/504 H |
| 4,716,296 | 12/1987 | Bussiere et al. | 250/504 H |
| 5,184,044 | 2/1993 | Thomas | 313/638 |
| 5,385,344 | 1/1995 | Gonser | 250/504 R |
| 5,416,624 | 5/1995 | Kartensen | 359/114 |

Primary Examiner—Bruce C. Anderson
Attorney, Agent, or Firm—Alan S. Korman; John C. Thompson

[57] ABSTRACT

A hand-held light curing device has a light source and a light guiding device having a light receiving opening. A lens arrangement with a focusing lens is positioned between the light source and the light guiding device. The focusing lens has first and second cut-off filters on proximal and distal surfaces thereof, respectively. The cut-off filters are preferably vapor-deposited on the surfaces. Preferably, the focusing lens has a convex surface facing the light source, and the first filter has reflective properties with respect to infrared light.

13 Claims, 2 Drawing Sheets

LIGHT CURING DEVICE

CROSS-REFERENCE TO RELATED APPLICATIONS

The present application is continuation-in-part of U.S. patent application Ser. No. 08/749,602 filed Nov. 18, 1996 abandoned, which in turn claims priority from German application no. 195 42 985.0 filed Nov. 17, 1995.

BACKGROUND OF THE INVENTION

The present invention relates to a light curing device, especially for irradiating curable dental compositions, with a light source and a light guiding device, such as a light guide, having a light receiving opening, whereby in the path of the light beam between light source and light receiving opening a focusing lens is arranged. The device is especially used for curing dental plastic materials that are polymerizable under the effect of light.

Such a light curing device is known from German Offenlegungsschrift 32 37 510. In such a light curing device the light source is surrounded by a reflector which focuses the emitted light radiation onto a focusing lens. The plano-convex focusing lens, the planar surface of which is facing the light source, is designed to focus the light beam onto the light receiving opening of the light guide. In the known light curing device spectral lamps are used as light sources, which are relatively large and heavy in order to be able to introduce monochromatic light radiation into the light guide.

In order to facilitate handling of the device, the known light curing device has a flexible light guide of a length of 2 meters. With this construction, the operator is thus limited in his moveability by the connection via the light guide. Furthermore, with a comparatively long and flexible light guide there is always present the danger of kinking. Even though possible external damages cannot be seen, the resulting light efficiency of the light guide is considerably reduced without being apparent to the operator.

However, this carries the considerable risk that a light curing step is not completed so that the used dental material is not cured according to specification.

Furthermore, hand-held devices are known, for example, from German Offenlegungsschrift 42 11 230. With such hand-held devices it is conventional to use, for the comparatively compact arrangement, light sources of high energy density which results often in thermal problems. Despite the comparatively high energy expenditure, the light efficiency for these hand-held devices is still improvable.

OBJECTS AND SUMMARY OF THE INVENTION

It is therefore an object of the present invention to provide a light curing device of the aforementioned kind that is improved with respect to light efficiency, is easier to manipulate, and provides a light efficiency that ensures complete polymerization over an extended service life.

Surprisingly, with the inventive, a favorable light efficiency with respect to light curing can be achieved despite the embodiment as a compact, hand-held device. Even though compact halogen universal lamps are used, which are considerably less expensive than spectral lamps, the light efficiency is surprisingly good and does not result in an undesirable heating within the mouth of the patient or with respect to the dental material to be cured. Apparently, the cut-off filter vapor-deposited onto the surface of the focusing lens facing the light source, has an especially good reflective effect for undesirable radiation without impairing the light radiation emitted by the halogen lamp. This cut-off filter has an especially good transmissivity for the frequency ranges required for polymerization. Advantageously, a light guide of a comparatively large diameter can be used whereby weight and handling problems of light guides of greater diameters are substantially reduced with respect to known light curing devices since the inventively used light guide extends only over a length of a few centimeters instead of being 1 to 2 meters long.

The inventive light curing device is especially advantageously realized as a hand-held device. Individual advantages result, however, also in an embodiment as a stationary device with flexible light guide.

The risk of unnoticed reduction of the light efficiently due to breakage of the light guide is practically prevented since the light guide can optionally be surrounded by a metal tube so as to be especially well protected since it must not be flexible.

According to a preferred embodiment, it is suggested to apply the cut-off filter onto the convex surface of the focusing lens. Inasmuch as heat radiation is reflected by the cut-off filter, the heat radiation is diverted which is especially favorable with respect to heat dissipation.

In an especially advantageous embodiment, the inventive light curing device comprises a reflector which is positioned adjacent to the focusing lens and/or cut-off filter whereby the reflector cone extends between the light source and a cut-off filter and/or the focusing lens and whereby the cone angle opens toward the light source. This reflector increases the light efficiency in that the radiation emitted by the light is reflected and guided toward the focusing lens and improves in a double function at the same time the heat dissipation of the cut-off filter, especially when the conical reflector sleeve comprises a metallic reflective layer.

According to another embodiment, the focusing lens is a plano-convex lens, the convex surface of which is especially facing the light source. This embodiment is especially favorable with respect to mounting and with respect to light introduction into the light guide. Light beams reflected by the light receiving opening are immediately reflected back at the planar surface of the focusing lens so that they can reenter the light guide.

When the focusing lens is made of heat-absorbing glass, the penetrating infrared radiation is mostly absorbed and the temperature is increased. In this context the focusing lens is spaced from the light guide so that there is no risk that the light guide is-heated to unacceptable limits. The absorption properties furthermore act to prevent the emission of heat radiation in the direction of the light guide.

It is understood that preferably both sides of the focusing lens are provided with vapor-deposited cut-off filters, with the filter facing the light source cutting off light at wavelengths higher than a predetermined wavelength, and the filter arranged distal from the light source cutting off light at wavelengths lower than a second predetermined wavelength, the light used for curing dental plastic materials falling within the bandwidth between the two filters.

Even though, in general, other methods for application of the cut-off filters are possible, it is preferred to vapor-deposit the cut-off filters. This allows for uniform and minimal layer thickness with optimal minimal transmission damping in the transmissive range of the filter.

It is understood that, if needed, the focusing lens can be used in combination with further lenses in order to improve the optical properties.

DETAILED DESCRIPTION

Figure 1:
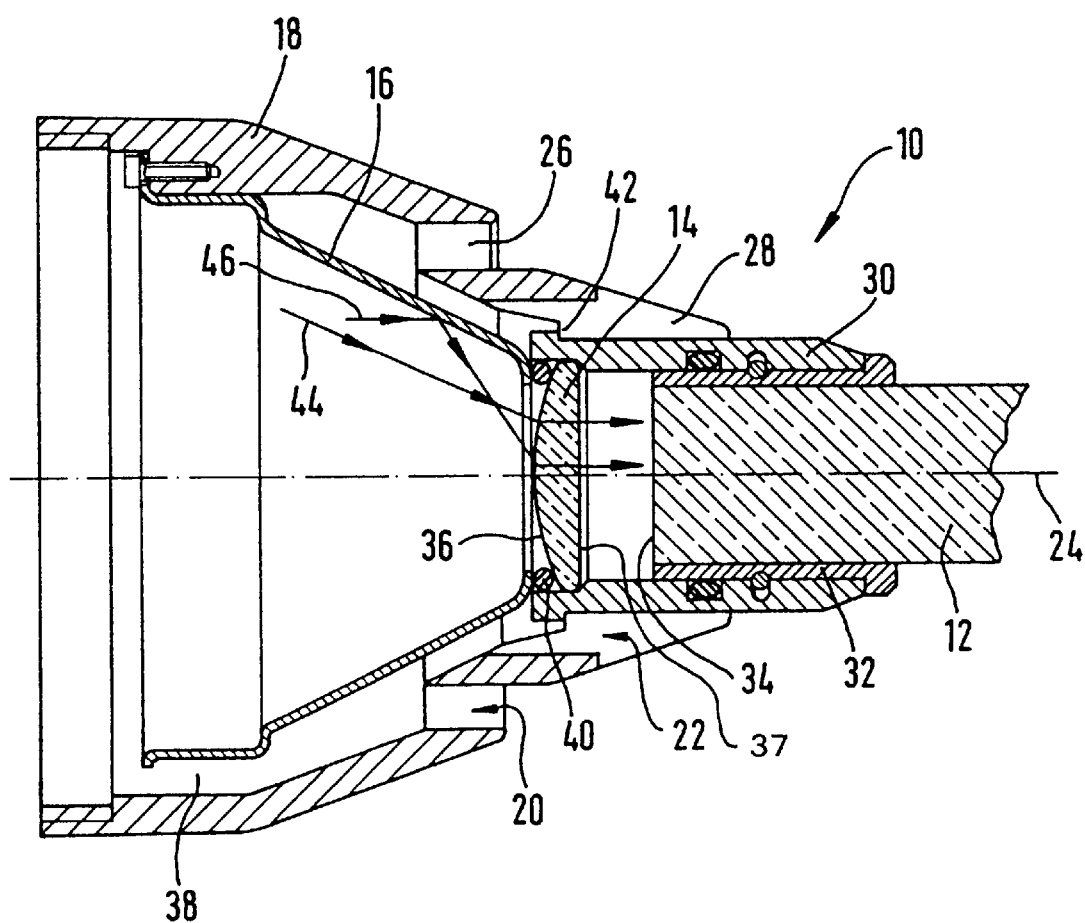
FIG. 1 shows a portion of the inventive light curing device in section, this view showing a plano-convex focusing lens and a light guide.

As apparent from FIG. 1, the inventive light curing device 10 comprises a light guide 12, a focusing lens 14, and a reflector 16 which are housed in a common housing 18. The housing 18 furthermore supports a light source (not shown) which can be optionally provided with a well known reflector and which would be positioned to the left in the drawing. The light guide 12 is only partly represented in the drawing and extends over a length of a few centimeters, optionally with a slightly bent tip, in order to allow easy access to any area within the mouth of a patient.

The light curing device is a hand-held device and has a construction as is, for example, known from German Offenlegungsschrift 42 11 230, the complete disclosure of which is herewith explicitly included by reference. The housing 18 comprises a plurality of vent openings 20, 22 which extend substantially annularly coaxially to the optical axis 24 and which are interrupted by ribs 26, 28 which are uniformly distributed over the circumference.

The housing is provided in a manner know per se with an exhaust fan (not shown) which is arranged behind a halogen lamp (not shown) and operated such that the vent openings 20, 22 act as air inlet openings. Thus, relatively cold air passes along the focusing lens 14 and the reflector 16 and provides a comparatively good cooling effect thereat. The focusing lens 14 is supported in the housing with a separate securing sleeve 30 which also supports the light guide 12. The light guide 12 is supported within the securing sleeve 30 by a socket 32. The arrangement of focusing lens 14 and light guide 12 within the securing sleeve 30 is selected such that the light receiving opening 34 of the light guide 12 is clearly spaced from the focusing lens 14. In the represented embodiment the spacing is greater than the maximal thickness of the focusing lens 14. The focus of the focusing lens 14 is positioned somewhat behind the light receiving opening 34 within the light guide 12.

As shown in FIG. 1, the focusing lens 14 is a plano-convex lens whereby the planar surface faces the light guide and the convex surface faces the light source. On the side facing the light source, a first cut-off filter 36 is vapor-deposited onto the lens, the filter cutting off light at wavelengths higher than a predetermined wavelength, preferably 500 nm. In addition, the lens is preferably comprised of heat-absorbing glass which absorbs to a large extent infrared radiation. Furthermore, on the side facing away from the light source, i.e., the distal side, a second cut-off filter 37 is vapor-deposited on the lens, the filter cutting off light at wavelengths lower than a predetermined wavelength, preferably 400 nm. Due to this arrangement, only light with the desired wavelength range can enter the light guide 12, for example, 400 to 500 nm. The rounded embodiment of the cut-off filter 36 also results in that the blocked light or radiation is reflected over a large surface area and distributed. The reflected radiation impinges on the reflector 16 which is positioned within the direct air flow at the flow channel 38 and which is thus cooled. Furthermore, the cut-off filter 36 and thus the focusing lens 14 are positioned in thermal vicinity of the reflector 16; via the vent openings 22 an additional flow channel which is directly adjacent is opened which participates in the cooling effect.

The support of the lens 14 is such that it is clamped with a securing ring 40, this is optionally elastic, between the securing sleeve 30 and the reflector 16. The reflector 16 is screwed from the interior onto the housing 18 so that the screw connection supports in sequence the securing sleeve 30, the focusing lens 14, the securing ring 40, and the reflector 16 at the corresponding securing flange 42 of the housing.

As can be seen in the drawing, the light radiation emitted by the light source is refracted partially directly, according to the course of the light beam 44, and then enters the light guide 12 parallel to the optical axis 24. Partly, the radiation is reflected at the reflector 16, as indicated by the light beam 46, enters the lens and, after corresponding refraction within the focusing lens 14, exits parallel to the optical axis 24. This is of course only true for light beams with wavelength which pass through the cut-off filter 36.

In the shown embodiment, the reflector 16 is a reflective metal part and has good heat conducting properties. However, it is understood that instead a plastic part with inner reflective layer can be used. It is advantageous to widen the reflector in the direction toward the light source.

Figure 2:
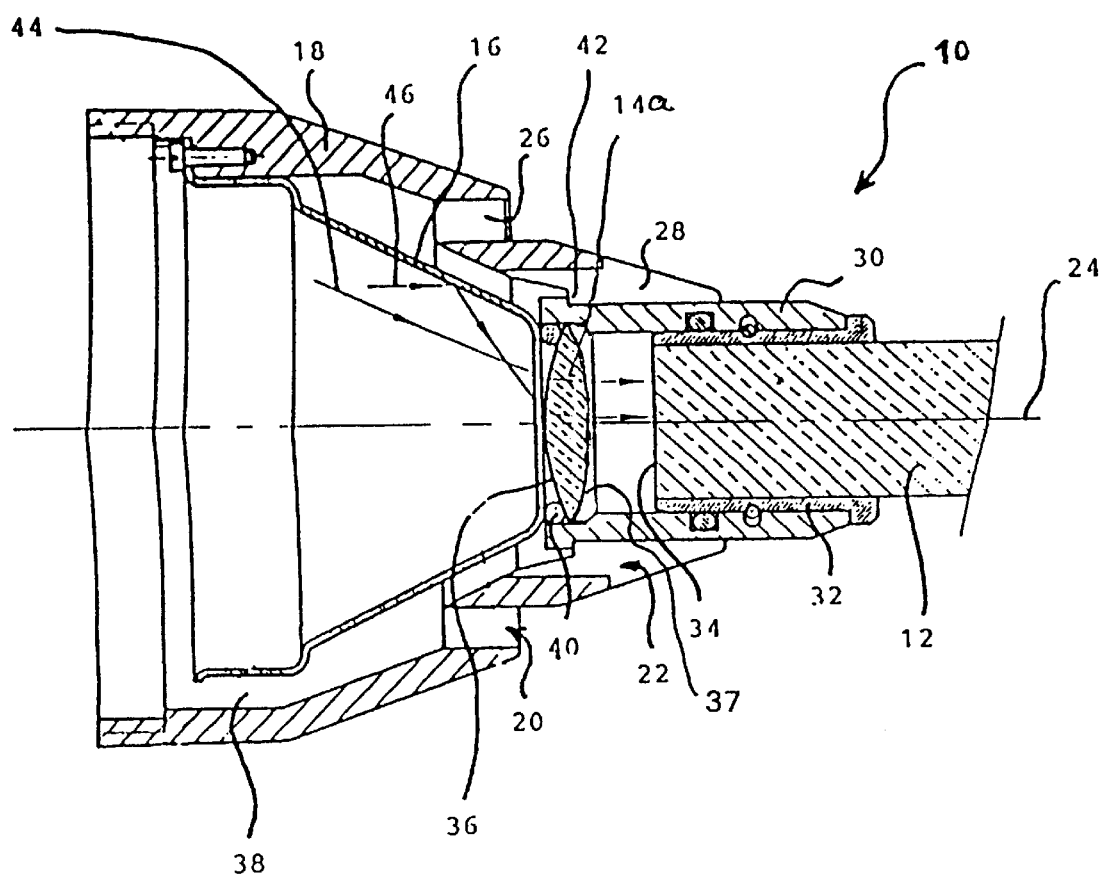
FIG. 2 is a view similar to FIG. 1 but showing a light curing ice provided with a biconvex lens.

With reference to FIG. 2, instead of the focusing lens 14, it is also possible to use a biconvex lens 14a arrangement. The focusing lens 14a is preferably provided with first and second cut-off filters 36, on the proximal and distal sides, the first filter cutting off wavelengths able a predetermined wavelength, and the second filter cutting off wavelengths below a predetermined wavelength in a manner similar to the FIG. 1 embodiment.

The present invention is, of course, in no way restricted to the specific disclosure of the specification and drawings, but also encompasses any modifications within the scope of the appended claims.

What is claimed is:

1. A hand-held light curing device comprising:
   a light source;
   a light guiding device having a light receiving opening;
   a lens arrangement comprising a focusing lens positioned between said light source and said light guiding device;
   said focusing lens comprising a first cut-off filter vapor-deposited on the surface of the lens proximal the light source and a second cut-off filter vapor-deposited on the distal surface of the lens, the first cut-off filter cutting off light at wavelengths higher than a predetermined wavelength and the second filter cutting off light at wavelengths lower than a predetermined wavelength.

2. A hand-held light curing device according to claim 1, wherein said focusing lens is a plano-convex lens having a convex surface, wherein said convex surface faces said light source.

3. A hand-held light curing device according to claim 1, further comprising a reflector comprising an inner surface with reflective coating, said reflector positioned adjacent to said focusing filter and widening conically in a direction toward said light source.

4. A hand-held light curing device according to claim 1, wherein said first cut-off filter has reflective properties with respect to blocked radiation.

5. A hand-held light curing device according to claim 1, wherein said focusing lens is spaced from said light guiding device and wherein a focus of said focusing lens coincides with said light receiving opening.

6. A hand-held light curing device according to claim 1, wherein said focusing lens is spaced from said light guiding device and wherein a focus of said focusing lens is positioned within said light guiding device.

7. A hand-held light curing device according to claim 1, wherein said light source is a compact lamp having a high light yield relative to a size of said lamp and relative to an amount of electric energy supplied to said lamp.

8. A hand-held light curing device according to claim 7, wherein said lamp is a halogen lamp.

9. A hand-held light curing device according to claim 1, wherein said lens arrangement further comprises a biconvex lens.

10. A hand-held light curing device according to claim 1, wherein said first cut-off filter is opaque to infrared radiation.

11. A hand-held light curing device according to claim 1, wherein said first cut-off filter allows light below a 500 nm wavelength threshold to pass.

12. A hand-held light curing device according to claim 1, wherein said second cut-off filter allows light above a 400 nm wavelength threshold to pass.

13. A hand-held light curing device according to claim 1, wherein said focusing lens consists of a heat-absorbing glass.

* * * * *